United States Patent [19]
Calderwood

[11] Patent Number: 5,700,085
[45] Date of Patent: Dec. 23, 1997

[54] SURGICAL OR CLINICAL LAMP HANDLE SHIELD OR PROPHYLACTIC

[76] Inventor: Mitchell C. Calderwood, 1801 State St., Suite D, Santa Barbara, Calif. 93101

[21] Appl. No.: 660,838

[22] Filed: Jun. 10, 1996

Related U.S. Application Data

[63] Continuation of Ser. No. 368,838, Jan. 5, 1995, abandoned.
[51] Int. Cl.$^6$ ............................................ F21L 15/12
[52] U.S. Cl. ........................... 362/399; 362/400; 362/804
[58] Field of Search ................................ 362/399, 400, 362/804; 206/223, 438; 150/155, 161, 163; 16/114 R, DIG. 12

[56] References Cited

U.S. PATENT DOCUMENTS

| | | | |
|---|---|---|---|
| 4,605,124 | 8/1986 | Sandel et al. | 206/223 |
| 4,777,574 | 10/1988 | Eisner | 362/399 |
| 4,976,299 | 12/1990 | Bickelman | 362/804 |
| 5,065,296 | 11/1991 | Cude | 362/399 |
| 5,156,456 | 10/1992 | Hoftman et al. | 16/114 R |

*Primary Examiner*—Y My Quach
*Attorney, Agent, or Firm*—Sanford J. Piltch

[57] ABSTRACT

A surgical or clinical lamp handle or adjusting means covering, barrier, shield or prophylactic comprised of a thin, tear-resistant elastic material which is disposable after a single use for covering the exposed surfaces of each of several different shaped and sized surgical or clinical lamp handles or adjusting means, as well as the handle or adjusting means elements which support and connect the handle or adjusting means to the surgical or clinical lamp for preventing the spread of infectious disease.

11 Claims, 2 Drawing Sheets

SURGICAL OR CLINICAL LAMP HANDLE SHIELD OR PROPHYLACTIC

CROSS-REFERENCE TO RELATED APPLICATION

This application is a continuation of U.S. patent application Ser. No. 08/368,838, filed Jan. 5, 1995, now abandoned.

BACKGROUND OF THE INVENTION

Operating room personnel have been aware for years that the repeated touching of the operating room or surgical lamp handle to redirect the illumination pattern or to bring the lamp closer to the area of concern, or to move the lamp farther away, can bring about the spread of contagious diseases through contact with the handle. Such contagious or communicable diseases are borne in or on the human body fluids and tissues which become attached to the exterior surfaces of the gloved (or ungloved) hands of operating personnel, doctors, nurses and other technicians, and are transmitted to the lamp handle or adjusting means through direct contact.

In the environment in which operating room personnel work, i.e. inside the human body, body fluids such as blood and the tissues comprising the organs, muscles and skin of the human body may potentially transmit a number of diseases and viral infections through contact. The process of surgery requires the incision or cutting into the body resulting in the outflow of blood and other body fluids as well as the scattering of various body tissues outside of the point of incision or cut. Some of such fluids and particles of tissues may become attached to the gloved hands of the operating room personnel. Cleaning and sterilization of the lamp handles or adjusting means has remained a serious problem for operating room and other hospital personnel because of their construction and the materials utilized to formulate the handle.

During operating procedures the lamp is almost continually repositioned for better lighting into the point of incision, the interior of the patient's body. The lamp handle is touched by a variety of operating room personnel in attempts to refocus the light onto the desired point of illumination on or in the body of the patient. Refocusing the light emitted by the lamp is accomplished with possibly contaminated exterior surfaces of the gloves worn by the operating room personnel who are still performing the surgical procedure. Anything such personnel may have come into contact with (known or unknown) while their gloved hands were in contact with the human patient will necessarily be transmitted to the surface of the lamp handle or other adjusting means upon touching the surface of such handle or adjusting means.

There have been some attempts to provide covers for surgical lamps for use in a surgical operatory. U.S. Pat. No. 4,777,574 [Eisner] discloses a thin, tear-resistant, semi-rigid but elastic material for covering the entirety of a variety of different types of dental surgical lamp adjusting means. The lamp handle shield of the Eisner patent is sufficiently flexible so as to stretch over a variety of different shaped handles. Another flexible surgical lamp handle cover is taught by U.S. Pat. Nos. 5,036,466 and 5,188,454 [Quintanilla, et al.]. These patents teach a semi-permanent, non-disposal surgical lamp handle cover which provides an asceptic medium for manual adjustment of the operating room lamp during surgical procedures. While the lamp cover of Eisner is disposable after each surgical procedure, the lamp handle cover of Quintanilla, et al. is described as semi-permanent in nature, although such cover can be disengaged and removed after each surgical procedure.

Semi-rigid surgical light handle covers are described in U.S. Pat. No. 4,559,671 [Andrews, et al.] and U.S. Pat. No. 4,605,124 [Sandel, et al.]. These patents disclose semi-rigid covers for principally protecting the grip portion of the handle of the surgical lamp, as well as an upward and radially outward extending projection which serves to prevent contact with the handle support elements of the surgical lamp.

Another semi-rigid surgical lamp handle cover is disclosed in U.S. Pat. No. 4,844,252 and Des. U.S. Pat. No. 313,670 [Barron, et al.]. The disclosure of the Barron, et al. patents teaches a multi-part disposable lamp handle for use on a surgical or operating room light. A similarly constructed device is disclosed in U.S. Pat. No. Des. 298,864 [Jefferson] which describes a disposable handle for operating room lights.

With the exception of the Eisner patent, all of the rest of the patents describe teachings of a variety of flexible or semi-rigid surgical lamp handle covers which may either be exchanged for the existing handle, cover the existing handle for one or more procedures, or cover the existing handle and be disposable after each procedure. The flexible or semi-rigid surgical lamp handle covers are flexible only to the extent that they are collapsible so as to be folded into a small container, bag or envelope, but in no way approach the flexibility of the material utilized in the Eisner teaching.

With reference to the lamp handle cover in the Eisner patent, the specific structure described and taught is for T-type and C-type shaped lamp handles. There is no enabling disclosure or teaching of a cover for an I-type or straight handle cover which has a radially outwardly extending upper portion to cover the handle support and lamp connection means for the handle for that type adjusting means for surgical or clinical lamps. Neither does the Eisner patent, or any of the other patents, suggest the substitution of the material used in the Eisner patent for the semi-rigid materials described as being used in the other cited patents.

Surgical or clinical lamps are not usually thought of as disease transmission devices. The lamps are usually cleaned, but not sterilized, after conclusion of a surgical procedure and before the next surgical procedure. Sterilization of the surgical (or clinical) lamp (and its handle or adjusting means), which is large and cumbersome to manipulate and usually mounted to the ceiling or wall of an operating or treatment room, is not easily accomplished as the sterilization which can be done with small surgical instruments. Although the lamp and its handle or adjusting means may be sprayed with a disinfecting agent, such practice does not entirely eliminate bacterial or viral forms on the lamp. Thus, attempted disinfection of the lamp between patients does not entirely create a sterile field and the surgical or clinical lamp (and its handle or adjusting means) may continue to be a disease transmission device.

It is, therefore, an object of the present invention to provide a clean or sterile field around an operating room (surgical) or treatment (clinical) lamp handle or adjusting means in order to alleviate, or entirely eliminate, the task of removal and sterilization of the handles or adjusting means.

It is a further object of the present invention to alleviate or entirely eliminate, significantly increased inventory costs by providing a single barrier which will fit over a broad spectrum of differently shaped handle or adjusting means and accommodate both the shape and size of the handle or adjusting means for both operating room and other healthcare settings where surgical or clinical lamps are operated and clean or sterile fields are required.

It is another object of the present invention to provide a barrier or shield which is highly elastic and stretchable, yet tear-resistant, and which is capable of covering the handle or adjusting means of the surgical or clinical lamps regardless of different shapes and sizes of those handles or adjusting means.

It is still a further object of the present invention to provide a barrier or shield which is disposable after a single use and which is easily applied and removed so that the barrier or shield will have greater acceptance among users in the healthcare field.

Other objects will appear hereinafter.

SUMMARY OF THE INVENTION

The surgical or clinical lamp handle or adjusting means covering, barrier, shield or prophylactic of the present invention is comprised of a thin, tear-resistant elastic material which is disposable after a single use for covering the exposed surfaces of each of several different shaped and sized surgical or clinical lamp handles or adjusting means, as well as the handle or adjusting means supports which support and connect the handle or adjusting means to the surgical or clinical lamp.

The present invention may be described as a disposable sterile surgical or clinical lamp shield or prophylactic for placement over and in proximate contact with the means for adjusting the illuminated focal point of said lamp for significantly reducing the spread of communicable and infectious diseases which may be transmitted by or through contact with human body fluids and tissues during a first and subsequent use of said lamp and its adjusting means in conjunction with the treatment of two or more patients. The use of such barrier will eliminate the need for repeated sterilization of the lamp and its adjusting means between such uses for the two or more patients.

The invention may be particularly described as comprising an elongated substantially cylindrical lower gripping portion conjoined to an inverted conically shaped upper flange portion terminating in a substantially circular aperture surrounded by a stiffening radial rib means for fitting over the lamp adjusting means and clinical lamp adjusting means supports to provide a gripping portion of the clinical lamp adjusting means without contamination of other surfaces of said lamp. The shield or prophylactic to fully accomplish its intended purpose has sufficient elastic material memory to maintain itself in position covering said adjusting means without slippage until manual removal. The shield or prophylactic has a preferred thickness in the range between 0.5 and 10 mils with the outer surface of the shield or prophylactic having a medium to high degree of frictional contact. The shield or prophylactic may be made from an elastomeric or elastic material, natural or man-made, or any combination thereof, with the material exhibiting sufficient deformability to stretch over the clinical lamp adjusting means, toughness and/or tear-resistance to withstand pulling and stretching during application and/or removal and material memory to return to and/or retain its original size and shape after application and/or removal.

The invention also contemplates a method for applying and removing a disposable sterile surgical or clinical lamp shield or prophylactic for providing a barrier to infectious disease contamination by the means for adjusting the illuminated focal point of said lamp which may be transmitted by or through contact with human body fluids and tissues during a first and subsequent use of said lamp and its adjusting means in conjunction with the treatment of two or more patients. This, again, eliminates the need for repeated sterilization of the lamp and its adjusting means between such uses for the two or more patients. The method includes the steps of providing a shield or prophylactic having an elongated substantially cylindrical lower gripping portion conjoined to an inverted conically shaped upper flange portion terminating in a substantially circular aperture surrounded by a stiffening radial rib means for fitting over the lamp adjusting means and lamp adjusting means supports to permit gripping of the lamp adjusting means without contamination of other surfaces of the lamp; mounting the shield or prophylactic over a hollow cylindrically shaped applicator means by stretching the lower gripping portion over a first end and the outside of the applicator means so a substantial portion of the lower gripping portion overlies the exterior of the applicator means with the interior surface of the lower gripping portion of the shield or prophylactic facing outward and the remaining portion of the lower gripping portion folded over the inside out portion of the lower gripping portion such that the upper flange portion is positioned proximally to the first end of the applicator means; applying the shield or prophylactic to the lamp adjusting means by unrolling the stretched and mounted shield or prophylactic by centering the applicator means adjacent the distal end of the lamp adjusting means and passing the applicator means upward over the lamp adjusting means of the lamp so as to stretch the shield or prophylactic completely over the lamp adjusting means; and maintaining the shield or prophylactic in position covering the lamp adjusting means without slippage until manual removal.

The protection may be enhanced by stretching the radial rib of the upper flange portion of the shield or prophylactic over surfaces adjacent to the lamp adjusting means which connect the lamp adjusting means to the lamp to cover the surfaces and to further secure the shield or prophylactic in position.

BRIEF DESCRIPTION OF THE DRAWINGS

For the purpose of illustrating the invention, there is shown in the drawings forms which are presently preferred; it being understood, however, that the invention is not limited to the precise arrangements and instrumentalities shown.

DETAILED DESCRIPTION OF THE INVENTION

The following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

Figure 1:
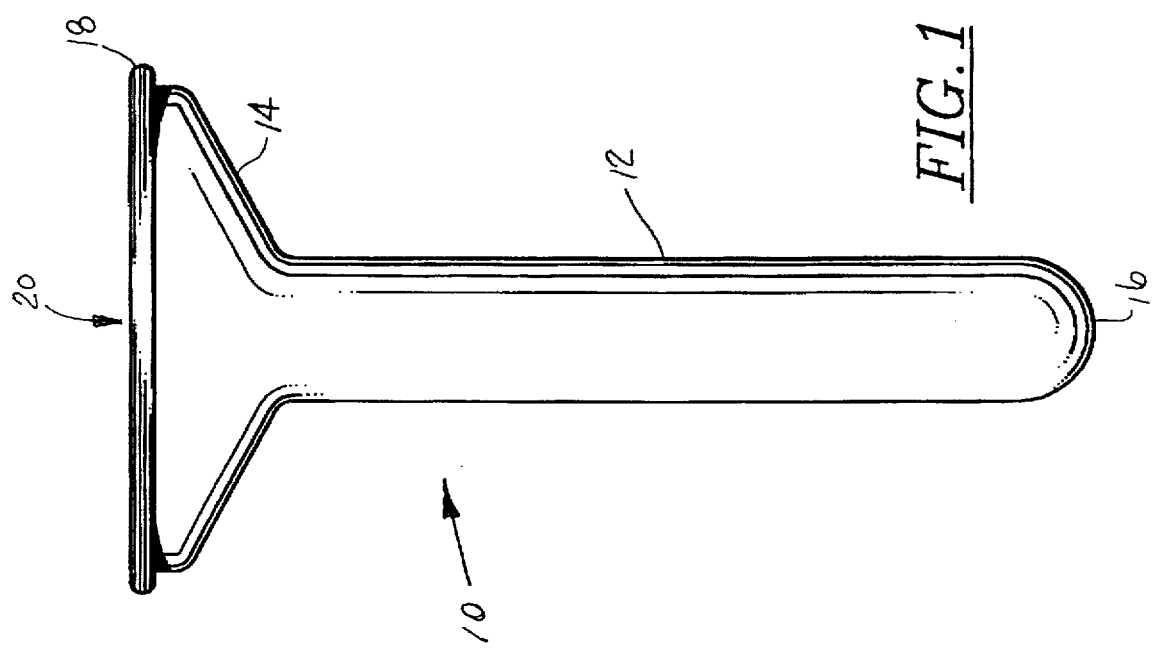
FIG. 1 is a side elevational view of the prophylactic cover of the present invention showing the cover fully extended.

Referring now to the drawings in detail, where like numerals refer to like parts or elements, there is shown in FIG. 1, a surgical or clinical lamp handle or adjusting means cover 10. The cover 10 may be referred to hereinafter as a shield, a barrier, or a prophylactic cover, all of which are to be understood as having the identical meaning.

The prophylactic cover 10 is shown in FIG. 1 in a fully extended position, although there is no radially outward flexion or extension, as the material from which the barrier 10 is made is in a relaxed state. The barrier or shield 10 may be formed from any elastomeric or elastic material, natural or man-made, or any combination thereof. The elastomeric or elastic material should exhibit sufficient deformability to stretch over a variety of differently shaped and sized surgical or clinical lamp handle or adjusting means and exhibit sufficient toughness and/or tear-resistance to withstand pulling and stretching during application and/or removal. The barrier or shield 10 should also exhibit sufficient material memory to return to and/or retain its original size and shape after application and/or removal. The outer surface of the barrier or shield 10 is preferred to have a medium to high degree of frictional contact to provide sufficient firmness of grasp during surgical or clinical procedures where hands, gloved or ungloved, may be slippery from contacting body fluids or otherwise.

The barrier, shield or prophylactic cover 10 of the present invention is generally comprised of a lower portion 12 and an upper portion 14. The lower portion 12 of the cover 10 preferably has a shape corresponding to an elongated cylinder having a closed first or bottom end 16 with the opposite end of the elongated cylindrical segment of the lower portion 12 conjoined to an equal sized substantially circular opening of the upper portion 14. The upper portion 14 is shaped substantially in the form of an inverted cone having a truncated vertex which meets and is joined to the substantially circular opposite end of the elongated cylindrical shaped segment of the lower portion 12. The inverted conically shaped upper portion 14 terminates in a radial rib or rim 18 which surrounds the upper open end 20 of the cover 10. The radial rib 18 completely circumscribes the opening or aperture 20 of the cover 10 and is generally formed from material which is permitted to overroll itself to form the stiffening rib (rim) 18 surrounding the upper opening 20.

Figure 2:
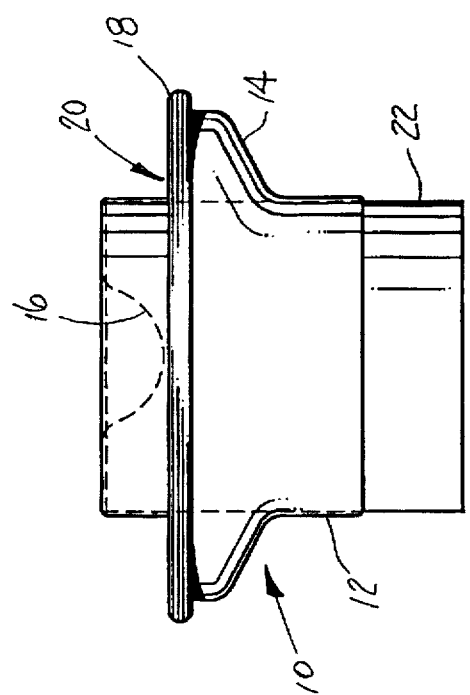
FIG. 2 is a side elevational view of the prophylactic cover of the present invention showing the cover mounted over an applicator means for placement of the cover over the surgical or clinical lamp handle or adjusting means.

With reference to FIG. 2, the apparatus of the present invention, the barrier, shield or prophylactic cover 10, is shown mounted over an applicator means 22 for use in more easily placing the cover 10 over a variety of differently shaped and sized handles or adjusting means of surgical or clinical lamps. The applicator means 22 is shaped in the form of a hollow cylinder, having interior and exterior surfaces, and may take the form of a plastic or paper expansion ring or tube. The applicator means 22 has equally sized open ends for ease of application of the cover 10 to the lamp handle or adjustment means 24 for lamp handles having a diameter smaller than the diameter of the applicator means 22.

The cover 10 placed over a first end of the applicator means 22 and partially stretched inside out over the exterior of the applicator means 22 so that substantially all of the lower (or grip) portion 12 overlies the exterior of the cylindrically shaped applicator means 22 with its interior surface facing outward. The remainder of the lower (or grip) portion 12 of the cover 10 is folded back over itself so that the upper portion 14 of the cover 10 is positioned just below the first end of the applicator means 22 over which the lower portion 12 has been stretched. The stretching of the lower (or grip) portion 12 of the cover 10 over the first end of the applicator means 22 does not deform (by stretching) the bottom end 16 of the barrier 10, as such bottom end 16 is useful as a centering point when applying the barrier 10 over one of a variety of differently shaped and sized lamp handle or adjusting means 24. The upper opening 20 of the barrier 10 is positioned closely proximate to the first end of the applicator means 22 as shown in FIG. 2.

Figure 3:
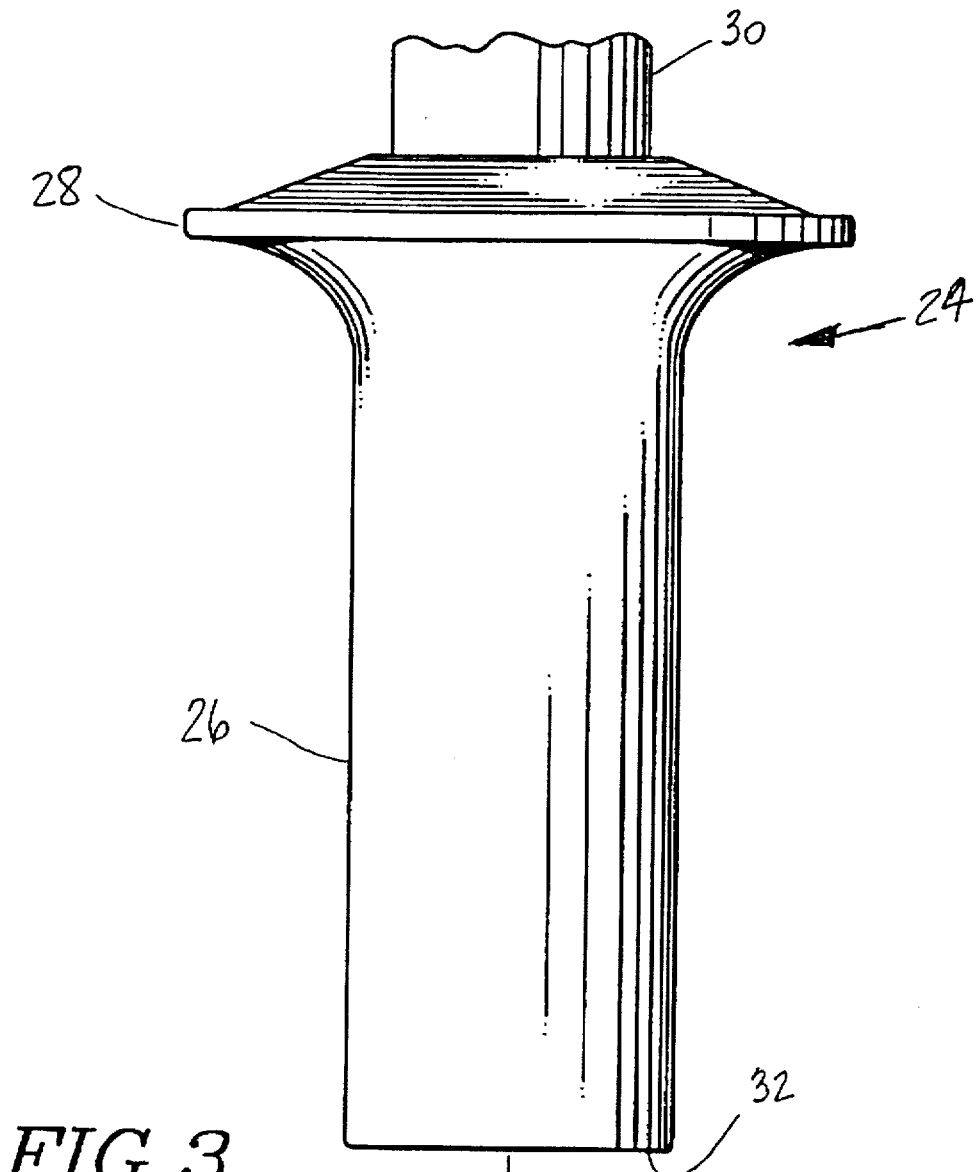
FIG. 3 is a side elevational view of the prophylactic cover of the present invention showing the cover mounted over the applicator means of FIG. 2 in position for application over one type of surgical or clinical lamp handle or adjusting means.

The placement or application of the barrier or shield 10 of the present invention can be best described with reference to FIG. 3. A lamp handle or adjustment means 24 is shown having an elongated cylindrical lower segment 26 and an outwardly flared upper segment 28 to provide a gripping surface for manual manipulation and aiming of the surgical or clinical lamp to which the lamp handle or adjustment means 24 is attached by the connection or support means represented as 30 in FIG. 3.

The applicator means 22 is positioned below the lamp handle or adjustment means 24 centering the bottom end 16 of the cover 10 under the elongated cylindrically shaped lower segment 26 of the lamp handle or adjustment means 24. Once the bottom end 16 of the barrier or shield 10 is positioned in contact with the distal end 32 of the lower segment 26 of the lamp handle or adjusting means 24, the applicator means 22 can be moved upward along the exterior of the lower segment 26 which causes the barrier or shield 10 to be pulled away from the applicator means 22 so as to roll and stretch over so as to overlie the lower segment 26 of the lamp handle or adjustment means 24 with the lower (or grip) portion 12 of the barrier or shield 10.

As the applicator means 22 approaches the upper or flared segment 28 of the lamp handle or adjustment means 24, the lower portion 12 of the barrier or shield 10 has been transferred from its folded overlying position over the exterior of the applicator means 22 and been rolled out and stretched over the lower segment 26 of the lamp handle or adjustment means 24 such that the upper portion 14 of the barrier or shield 10 is now positioned to contact and overlie the upper or flared segment 28 of the lamp handle or adjustment means 24. The upper (or flange) portion 14 of the barrier 10 provides protection against the gloved hand of any operating room personnel contaminating surfaces adjacent to the gripping portion of the lamp handle and adjusting means 24. The flange portion 14 is supported by the radial rib 18 and can be stretched radially outward so that the rib 18 can be positioned over a handle flange to provide a secure fit and complete barrier coverage of all elements of any lamp handle or adjusting means 24.

When the barrier or shield 10 is fully in position contacting and being stretched over the lower segment 26 and the upper or flared segment 28 of the lamp handle or adjustment means 24, the barrier or shield 10 is no longer in contact with the applicator means 22 and said applicator means 22 can be withdrawn by sliding downward and off of the now covered lamp handle or adjustment means 24. For proper placement and stretching of the cover 10 over the lamp handle or adjustment means 24, the diameter of the applicator means 22 is preferably in the range of ⅛" to ⅜" larger than the largest diameter measurement of any of the differently shaped and sized lamp handle or adjustment means 24. Thus, once the prophylactic cover 10 is positioned over the lamp handle or adjustment means 24 of a surgical or clinical lamp, the applicator means can be slid downward and off of the now covered lamp handle or adjustment means 24 and discarded.

Once positioned, the barrier, shield or prophylactic cover 10 protects against contamination and cross-contamination by the lamp handle or adjusting means 24 without such cover. Therefore, the application, by stretching the barrier, shield or prophylactic cover 10 over the lamp handle or adjustment means 24 of a surgical or clinical lamp, provides a barrier or shield to gross or microcontamination, or bacterial or viral contamination, of the lamp handle and proximal surgical or clinical lamp surfaces. Any contamination which occurs during a surgical procedure will remain on the exterior surface of the barrier, shield or prophylactic cover 10 and can be disposed of in the appropriate manner for suspected infectious waste and contaminated items by removing the cover 10 at the end of such treatment or procedure. Removal of the barrier or shield 10 is accomplished by rolling the barrier or shield 10 downward over itself and off of the lamp handle or adjustment means 24, and then discarding the cover 10 in an appropriate manner.

The shield, barrier or prophylactic cover 10 of the present invention is preferably manufactured from latex having a thickness in the range of 0.5 to 10 mils as this thickness is desired for the shield to exhibit the identified properties set forth above. Further, the barrier or shield 10 can be provided in either sterile or aseptic packaging depending upon its use in either a sterile field or in only a substantially clean and infection free environment.

The barrier, shield or prophylactic cover 10 of the present invention can be used with all presently manufactured shapes and sizes of surgical and clinical lamp handles or adjustment means due to its ability to adapt and/or conform to the variety of exterior shapes of these lamp handles or adjusting means. The present invention provides a significant step forward in the application and removal of such barriers, shields or prophylactic covers to reduce the spread of infectious or contagious and communicable diseases of either the bacteriological or viral type which are borne on the body fluids and tissues of humans. Without a barrier, shield or prophylactic cover of the present invention, the surgical or clinical lamp handle or adjusting means would be a likely place for the harboring and transmittances of infection and disease.

The present invention may be embodied in other specific forms without departing from the spirit or essential attributes thereof and, accordingly, the described embodiments are to be considered in all respects as being illustrative and not restrictive, with the scope of the invention being indicated by the appended claims, rather than the foregoing detailed description, as indicating the scope of the invention as well as all modifications which may fall within a range of equivalency which are also intended to be embraced therein.

I claim:

1. A disposable sterile surgical lamp shield for placement over and in proximate contact with a means for adjusting a surgical lamp in order to control an illuminated focal point produced by said lamp which significantly reduces the spread of communicable and infectious diseases which may be transmitted through contact with human body fluids and tissues during a first and subsequent use of said surgical lamp and said surgical lamp adjusting means in conjunction with the treatment of a plurality of patients eliminating the need for repeated sterilization of said surgical lamp and said surgical lamp adjusting means between such uses for the plurality of patients comprising an elongated substantially cylindrical lower gripping portion conjoined to an inverted conically shaped upper flange portion terminating in a stiffening radial rib means surrounding a substantially circular aperture defined by said upper flange portion, said radial rib means being expandable, for fitting over surgical lamp adjusting means of various sizes and surgical lamp adjusting means supports of various sizes, which connect said surgical lamp adjusting means to said surgical lamp, to provide a gripping portion of the surgical lamp adjusting means without contamination of said surgical lamp, said surgical lamp shield having sufficient elastic material memory to maintain itself in position covering said surgical lamp adjusting means without slippage until manual removal.

2. In accordance with claim 1, said shield having a thickness in the range between 0.5 and 10 mils.

3. In accordance with claim 1, wherein the surgical lamp shield has an outer surface which outer surface has a medium to high degree of frictional contact.

4. In accordance with claim 1, wherein the surgical lamp shield is made from a group consisting of elastomeric material, elastic material, natural, man made and any combination thereof.

5. In accordance with claim 1, wherein the surgical lamp shield exhibits sufficient deformability to stretch over the surgical lamp adjusting means, toughness and tear-resistance to withstand pulling and stretching during application onto and removal from said surgical lamp adjusting means and material memory to return to its original size and shape after application onto and removal from said surgical lamp adjusting means.

6. A method for applying and removing a disposable sterile surgical lamp shield to a means for adjusting a surgical lamp in order to control an illuminated focal point produced by said lamp for providing a barrier to infectious disease contamination of said surgical lamp which may be transmitted through contact with human body fluids and tissues during a first and subsequent use of said surgical lamp and its adjusting means in conjunction with the treatment of a plurality of patients eliminating the need for repeated sterilization of said surgical lamp and its adjusting means between such uses for the plurality of patients comprising the steps of:

provideing a shield having an elongated substantially cylindrical lower gripping portion conjoined to an inverted conically shaped upper flange portion terminating in a substantially circular aperture surrounded by a stiffening radial rib means of said shield for fitting over the lamp adjusting means and lamp adjusting means support, which connect said surgical lamp adjusting means to said surgical lamp, to permit gripping of the lamp adjusting means at a proximal end without contamination of said surgical lamp;

mounting said surgical lamp shield over a hollow cylindrically shaped applicator means by stretching the lower gripping portion of said surgical lamp shield over a first end of an outer surface of said applicator means so that a substantial portion of said shield overlies the outer surface of the applicator means with an interior surface of the lower gripping portion of said surgical lamp shield facing outward and the remaining portion of the lower gripping portion folded over the interior surface of the lower gripping portion such that the upper flange portion is positioned proximally to the first end of the applicator means;

applying said surgical lamp shield to said surgical lamp adjusting means by unrolling the stretched and mounted surgical lamp shield by centering the applicator means adjacent a distal end of the surgical lamp adjusting means and sliding the applicator means over the surgical lamp adjusting means of said surgical lamp so as to stretch said surgical lamp shield completely over said lamp adjusting means;

maintaining said shield in position covering said surgical lamp adjusting means without slippage until manual removal.

7. The method of claim 6 further comprising the step of stretching the radial rib means of the upper flange portion of said surgical lamp shield over the surgical lamp adjusting means support, adjacent to said surgical lamp adjusting means, in order to cover said lamp adjusting means support and to further secure said surgical lamp shield in position.

8. In accordance with the method of claim 6, wherein said surgical lamp shield has a thickness in the range between 0.5 and 10 mils.

9. In accordance with the method of claim 6, wherein the surgical lamp shield has an outer surface which outer surface has a medium to high degree of frictional contact.

10. In accordance with the method of claim 6, wherein the surgical lamp shield is made form a group consisting or elastomeric or elastic material, natural, man-made and any combination thereof.

11. In accordance with the method of claim 6, wherein the surgical lamp shield exhibits sufficient deformability to stretch over said surgical lamp adjusting means, toughness and tear-resistance to withstand pulling and stretching during application onto and removal from said surgical lamp adjusting means, and material memory to return to and retain its original size and shape after application onto and removal from said surgical lamp adjusting means.

* * * * *